(12) United States Patent
Al-Salem

(10) Patent No.: US 10,364,395 B2
(45) Date of Patent: Jul. 30, 2019

(54) PYROLYSIS REACTOR SYSTEM FOR THE CONVERSION AND ANALYSIS OF ORGANIC SOLID WASTE

(71) Applicant: KUWAIT INSTITUTE OF SCIENTIFIC RESEARCH, Safat (KW)

(72) Inventor: Sultan Al-Salem, Safat (KW)

(73) Assignee: Kuwait Institute for Scientific Research, Safat (KW)

( * ) Notice: Subject to any disclaimer, the term of this patent is extended or adjusted under 35 U.S.C. 154(b) by 119 days.

(21) Appl. No.: 15/487,351

(22) Filed: Apr. 13, 2017

(65) Prior Publication Data

US 2018/0298285 A1 Oct. 18, 2018

(51) Int. Cl.
| | |
|---|---|
| C10B 47/02 | (2006.01) |
| C10B 47/04 | (2006.01) |
| C10B 47/06 | (2006.01) |
| G01N 30/06 | (2006.01) |
| G01N 30/12 | (2006.01) |
| C10B 53/07 | (2006.01) |

(Continued)

(52) U.S. Cl.
CPC .............. C10B 53/07 (2013.01); C10B 53/00 (2013.01); G01N 31/12 (2013.01); C10B 47/02 (2013.01);
(Continued)

(58) Field of Classification Search
CPC ......... C10B 53/00; C10B 53/02; C10B 53/04; C10B 53/07; C10B 53/08; C10B 47/02;
(Continued)

(56) References Cited

U.S. PATENT DOCUMENTS 3,746,509 A 7/1973 Koskan
4,426,936 A * 1/1984 Kuo .................. B01J 8/002
110/221
(Continued)

FOREIGN PATENT DOCUMENTS

CN 105606430 A 5/2016
JP 63-25550 A 2/1988
(Continued)

OTHER PUBLICATIONS

Hinshaw, "Valves for Gas Chromatography: Fundamentals", Mar. 1, 2011, LCGC North America, vol. 29, Issue 3, p. 246-251, availabe online at: http://www.chromatographyonline.com/valves-gas-chromatography-fundamentals-1.*
(Continued)

*Primary Examiner* — Jonathan Miller
*Assistant Examiner* — Jonathan Luke Pilcher
(74) *Attorney, Agent, or Firm* — Richard C. Litman

(57) ABSTRACT

The pyrolysis reactor system for the conversion and analysis of organic solid waste is a dual gas-liquid separation system, allowing for the conversion of organic solid waste, as well as analysis of the conversion products. A pyrolysis reactor is provided for converting the organic solid waste into a solid product and a gas-liquid product mixture through pyrolysis. A source of carrier gas is in fluid communication with the pyrolysis reactor for degrading the organic solid waste. A first gas-liquid separator is in fluid communication with the pyrolysis reactor and receives the gas-liquid product mixture therefrom, separating a portion of gas therefrom. A second gas-liquid separator is in fluid communication with the first gas-liquid separator and receives the gas-liquid product mixture therefrom and separates the remainder of the gas therefrom. The remainder of the gas and the separated liquid (Continued)

are each collected separately from one another, in addition to the char.

4 Claims, 1 Drawing Sheet

(51) Int. Cl.
    *C10B 53/00*     (2006.01)
    *G01N 31/12*     (2006.01)

(52) U.S. Cl.
    CPC .............. *C10B 47/04* (2013.01); *C10B 47/06* (2013.01); *G01N 30/06* (2013.01); *G01N 30/12* (2013.01); *G01N 2030/125* (2013.01); *G01N 2030/126* (2013.01); *Y02E 50/14* (2013.01); *Y02P 20/143* (2015.11); *Y02P 30/20* (2015.11)

(58) Field of Classification Search
    CPC ......... C10B 47/04; C10B 49/02; C10B 47/06; C10B 47/16; C10B 47/00; C10B 49/00; C10L 2290/60; C10J 2300/1269; C10J 2300/1276; C10J 3/02–44; G01N 2030/125; G01N 2030/126; G01N 2030/062; G01N 30/06; G01N 30/12; G01N 2030/123; C10G 1/02; C10G 1/10
    See application file for complete search history.

(56) References Cited

U.S. PATENT DOCUMENTS

| | | | | |
|---|---|---|---|---|
| 4,746,406 A | * | 5/1988 | Timmann | ................ C10B 47/24 201/25 |
| 8,317,883 B1 | * | 11/2012 | Boateng | .................... C10L 1/02 44/307 |
| 8,382,957 B2 | * | 2/2013 | Farneman | .............. B01J 19/126 202/100 |
| 9,200,207 B2 | * | 12/2015 | Huang | .................... C10G 1/002 |
| 9,434,885 B2 | * | 9/2016 | Mullen | .................... C10B 53/02 |
| 2008/0141589 A1 | * | 6/2008 | Farneman | .............. B01J 19/126 48/197 FM |
| 2010/0275514 A1 | * | 11/2010 | Paganessi | .................. C10J 3/20 48/86 R |
| 2012/0172622 A1 | | 7/2012 | Kocal | |
| 2012/0310023 A1 | * | 12/2012 | Huang | .................. C10G 1/002 585/241 |
| 2013/0144095 A1 | * | 6/2013 | Farneman | ................ C10G 1/10 585/241 |
| 2014/0238835 A1 | * | 8/2014 | Mullen | .................... C10B 53/02 201/14 |
| 2015/0218457 A1 | | 8/2015 | Jacobsen | |
| 2015/0321980 A1 | * | 11/2015 | Levin | ...................... C10B 49/22 568/881 |
| 2016/0097002 A1 | | 4/2016 | Sundaram | |
| 2016/0186079 A1 | | 6/2016 | Xu et al. | |
| 2017/0009141 A1 | * | 1/2017 | Datta | ...................... C10B 49/14 |

FOREIGN PATENT DOCUMENTS

| | | |
|---|---|---|
| JP | 7-198703 A | 8/1995 |
| JP | 2011-149844 A | 8/2011 |
| WO | 2016200262 A1 | 12/2016 |

OTHER PUBLICATIONS

"Efficient Automated Pyrolysis GC," GERSTEL Solutions Worldwide, Mar. 2009. 2 pages, printed on Mar. 13, 2017.

* cited by examiner

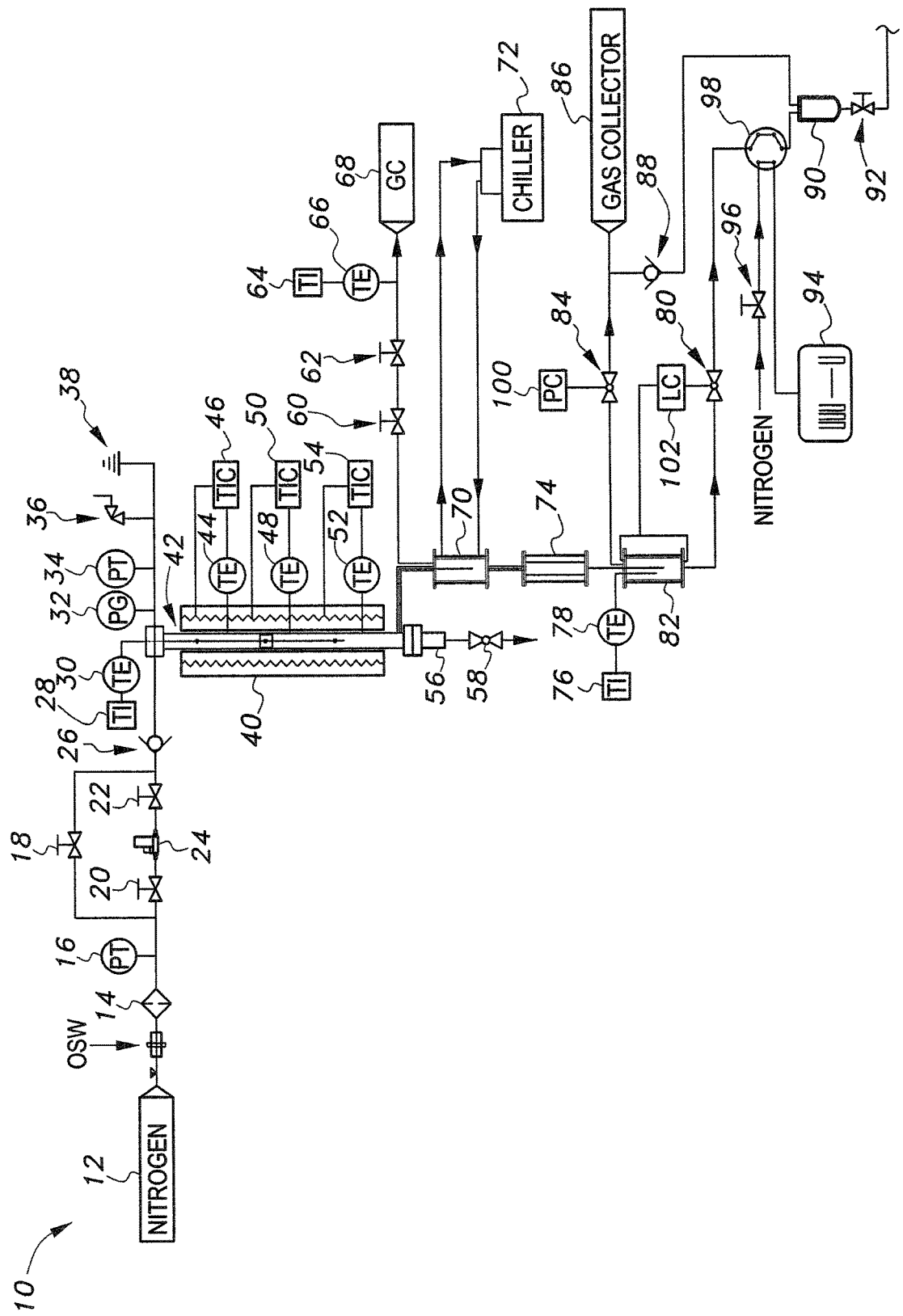

PYROLYSIS REACTOR SYSTEM FOR THE CONVERSION AND ANALYSIS OF ORGANIC SOLID WASTE

BACKGROUND OF THE INVENTION

1. Field of the Invention

The present invention relates to pyrolysis reactors, and particularly to a pyrolysis reactor system for the conversion and analysis of organic solid waste.

2. Description of the Related Art

Pyrolysis is the thermochemical decomposition of organic material at elevated temperatures in the absence of oxygen (i.e., an inert atmosphere). It involves the simultaneous changes of the chemical composition and physical phase in an irreversible reaction. Specifically, pyrolysis is a type of thermolysis and is most commonly observed in organic materials exposed to high temperatures, such as the process of treating cellulose and thermoplastics. In general, pyrolysis of organic substances produces gas and liquid products and leaves a solid residue richer in carbon content, referred to as "char". Extreme pyrolysis, which leaves mostly carbon as the residue, is called carbonization.

Pyrolysis is used heavily in the chemical industry, for example, to produce charcoal, activated carbon, methanol and other chemicals from wood, to convert ethylene dichloride into vinyl chloride to make polyvinyl chloride (PVC), to produce coke from coal, to convert biomass into syngas and biochar, to turn waste plastics back into usable oil or polymeric waste into safely disposable substances, and for transforming medium-weight hydrocarbons from oil into lighter ones, such as gasoline. Pyrolysis differs from other processes, such as combustion and hydrolysis, in that it usually does not involve reactions with oxygen, water or any other reagents.

Although both applied pyrolysis (i.e., conversion of organic material for a practical purpose) and analytical pyrolysis (i.e., conversion of organic material to study the chemistry and thermodynamics thereof) are well known and well-practiced, the two processes are presently carried out separately, the former being mainly an industrial process and the latter being a laboratory based process. It would be desirable, for purposes of research, to be able to perform applied pyrolysis processes, as they would be performed in actual applications, while simultaneously performing analysis. It would be further desirable to provide a process for treating material feedstock in various quantities, allowing for scale-up if desired by the user. Thus, a pyrolysis reactor system for the conversion and analysis of organic solid waste solving the aforementioned problems is desired.

SUMMARY OF THE INVENTION

The pyrolysis reactor system for the conversion and analysis of organic solid waste is a dual gas-liquid separation system, allowing for the conversion of organic solid waste, such as plastics, biomass, municipal solid waste, etc., as well as analysis of the conversion products. A pyrolysis reactor is provided for converting the organic solid waste into a solid product and a gas-liquid product mixture through pyrolysis. A source of carrier gas, such as nitrogen or any other suitable non-reactive gas, surrounds the pyrolysis reactor, ensuring pyrolytic conditions. A first gas-liquid separator is in fluid communication with the pyrolysis reactor for receiving the gas-liquid product mixture therefrom and separating a portion of gas therefrom. The portion of gas is output from the first gas-liquid separator for analysis thereof by gas chromatography or the like. A second gas-liquid separator is in fluid communication with the first gas-liquid separator for receiving the gas-liquid product mixture therefrom and separating a remainder of the gas therefrom. The remainder of the gas and the separated liquid are each collected separately from one another for analysis thereof.

In operation, the organic solid waste is fed into the pyrolysis reactor under the flow of the carrier gas. Pyrolysis is performed on the organic solid waste to convert the organic solid waste into a solid product and a gas-liquid product mixture, each of which are then extracted from the pyrolysis reactor. The first gas-liquid separator separates a portion of gas from the gas-liquid product mixture for analysis of its components by gas chromatography or the like. The second gas-liquid separator separates a remainder of the gas from the gas-liquid product mixture for collection thereof and analysis of its components. The liquid separated from the gas-liquid product mixture may be fractionated, stored and analyzed. Any remaining gas mixed with the liquid sample is drawn off and mixed with the gas initially separated by the second gas-liquid separator for storage and analysis. Although the pyrolysis reactor system for the conversion and analysis of organic solid waste may be used with any suitable type of organic and/or polymeric solid waste, as an example, if the organic solid waste is a polyolefin, one may expect the resultant pyrolysis products to include ethane, ethane, propene and propane. If end of life tires (ELTs) are to be used and treated, one may epect styrene, butadiene and polyaromatics.

The pyrolysis reactor is of the fixed bed batch reactor type with a three-zone temperature furnace associated therewith. For purposes of study and analysis, one or more of the three zones of the pyrolysis reactor is selected for performance of the pyrolysis, and each of the three zones preferably operates at a unique temperature up to 850° C.

These and other features of the present invention will become readily apparent upon further review of the following specification and drawings.

BRIEF DESCRIPTION OF THE DRAWINGS

The sole drawing FIGURE is a schematic diagram of a pyrolysis reactor system for the conversion and analysis of organic solid waste according to the present invention.

DETAILED DESCRIPTION OF THE PREFERRED EMBODIMENTS

The pyrolysis reactor system for the conversion and analysis of organic solid waste 10 is a dual gas-liquid separation system, allowing for the conversion of organic solid waste, such as plastics, biomass, municipal solid waste, etc. as well as analysis of the conversion products. As shown in the sole drawing FIGURE, a pyrolysis reactor 40 is provided for converting the organic solid waste (OSW) into a solid product and a gas-liquid product mixture through pyrolysis. It should be understood that any suitable type of pyrolysis reactor may be utilized, such as the conventional cylindrical, packed bed reactor 40 shown in the sole drawing FIGURE, which is coupled with a conventional three-zone furnace, heated by three separate temperature elements (TEs) 44, 48, 52, which are each respectively under the control of conventional temperature indicators/controllers (TICs) 46, 50, 54. The use of the conventional three-zone furnace allows for experimentation under varying temperatures and at varying points. TICs 46, 50, 54 may be thermocouples or the like. Each of the three zones may be selectively heated up to 850° C. Preferably, the pyrolysis reactor system for the conversion and analysis of organic solid waste 10 is scalable and allows for the treatment of different quantities of feedstock, preferably ranging from batches of 100 g to 600 g. The pyrolysis reactor system for the conversion and analysis of organic solid waste 10 can further preferably also handle a packing material, such as, for example, alumina packing.

As in a conventional pyrolysis reaction system, a source of carrier gas 12, such as nitrogen or any other suitable non-combustible gas, is in fluid communication with the pyrolysis reactor 40 for delivering the organic solid waste (OSW) into the pyrolysis reactor 40. As in a conventional pyrolysis reaction system, the organic solid waste may be fed into the carrier stream (and, ultimately, the reactor 40) by any suitable type of feed hopper or the like. As shown in the sole drawing FIGURE, additional components may be utilized in the feed, such as a filter 14 allowing for separation out of material by size or type, as well as a pressure monitor, such as a pressure transducer (PT) or transmitter 16, allowing for active monitoring of the nitrogen pressure. A mass flow controller 24 may be further provided, allowing for the selective control over the flow rate of the organic solid waste (carried by the nitrogen gas). In the sole drawing FIGURE, the mass flow controller 24 is shown in communication with conventional needle valves 18, 20, 22 for controlling, at these points, the flow toward reactor 40. In this way, the mass flow can be controlled between 0 to 500 mL/min.

Additionally, a check valve 26 or the like may be provided to prevent backflow from the reactor 40. As the organic solid waste is fed into feed bed 42 of the reactor 40, pre-heating thereof may be controlled by a further temperature element 28 and monitored by a corresponding temperature indicator (TI) 28. Pressure at the feed point may also be monitored by a pressure gauge (PG) 32, a pressure transducer or transmitter 34, or the like. Additionally safety measures, such as pressure safety or pressure relief valve 36 and/or a rupture disc 38, may also be provided in the feed line.

Following pyrolysis of the organic solid waste, the solid product (i.e., char and ash) is collected in a hopper 56 and may be dispensed by an isolation valve 58 or the like. A first gas-liquid separator 70 is in fluid communication with the pyrolysis reactor 40 for receiving the gas-liquid product mixture therefrom and separating a portion of gas therefrom. The portion of gas is output from the first gas-liquid separator 70 for analysis thereof by a gas chromatograph (GC) 68 or the like. As shown, flow of the portion of gas delivered to GC 68 may be controlled by needle valves 60, 62 or the like. Further, the temperature of the gas portion may be controlled by temperature element 66 and monitored by temperature indicator 64. It should be understood that any suitable type of gas-liquid separation may be used, such as cooled gas-liquid separation. In this example, a chiller 72 is in fluid communication with the first gas-liquid separator 70. The chiller 72 further acts to provide the gas sample to the gas chromatograph 68 at an acceptable temperature for analysis. In the sole drawing FIGURE, the first gas-liquid separator 70 is shown as a conventional cooled jacket type gas-liquid separator. In this example, service fluid is circulated through the jacket, in a conventional manner, with the service fluid being temperature controlled by the chiller 72, which may operate in a range of −40° C. to 180° C. This further serves as a primary temperature guard, thus reducing the load on the condenser 74 and second gas-liquid separator 82 (as will be described in greater detail below).

The gas-liquid mixture flows to a second gas-liquid separator 82, through the condenser 74 for full separation of the remainder of the gas from the liquid. It should be understood that any suitable type of condenser may be utilized. The condenser 74 is provided with sufficient heat transfer area to condense the product vapor delivered by the reactor 40 and the first gas-liquid separator 70. As with the first gas-liquid separator 70, the service fluid may be circulated into the condenser 74 in the range of −40° C. to 180° C. As shown, the gas is collected in a gas collector 86, and the flow thereto may be controlled and regulated by a back pressure regulator 84 or the like, which operates in conjunction with a pressure controller (PC) 100. Preferably, the second gas-liquid separator 82 is similar to the first gas-liquid separator 70, i.e., it may also be a conventional cooled jacket type gas-liquid separator. Here, the temperature of the circulating service fluid is selected based on the process requirements.

The separated liquid is also delivered to a sample collection vessel 90, and samples may be dispensed through a needle valve 92 or the like. As shown, liquid flow may be under the control of a liquid control valve 80, which may be directly monitored and controlled by a liquid controller (LC) 102 (monitoring and controlling temperature, pressure, flow rate, etc.). The liquid controller 102 preferably includes level monitoring, allowing the valve 80 to act as a level control valve, enabling liquid sampling at a desired rate and preventing flooding of the delivery tube.

As shown, a multi-port valve 98 may be provided for fractional separation of liquid components under nitrogen flow through a valve 96 for additional analysis of component fractions in a fraction collector 94. For example, a six-port valve may be used for automatic sampling of the liquid. When fractionation is desired, a sample collection vessel 90 is used to collect any excess product. As shown, any gases that may have been captured can exit the vessel 90, passing through a check valve 88 for collection in gas collector 86 for sampling thereof.

It should be understood that the pyrolysis reactor system for the conversion and analysis of organic solid waste 10 may be used with a wide variety of organic solid and/or polymeric waste products. Thus, the end products will vary significantly. For example, the gases collected in gas collector 86 may be light hydrocarbon gases, and the liquids collected in vessel 90 and/or fraction collector 94 may be in the form of heavy waxes and oils. As an example, if the organic solid waste is a polyolefin, one may expect the resultant pyrolysis products to include ethane, ethene, propene and propane. If end of life tires (ELTs) are to be used and treated, one may epect styrene, butadiene and polyaromatics. Additionally, as noted above, although the pyrolysis reactor 40 may be any suitable type of pyrolysis reactor, such as, for example, a conventional fixed bed, batch reactor, the furnace associated therewith is preferably a conventional three-zone furnace. For purposes of study and analysis, one of the three zones of the pyrolysis reactor is selected for performance of the pyrolysis, and each of the three zones preferably operates at a unique temperature up to 850° C.

It is to be understood that the present invention is not limited to the embodiments described above, but encompasses any and all embodiments within the scope of the following claims.

I claim:

1. A pyrolysis reactor system for the conversion and analysis of organic solid waste, comprising:
   a pyrolysis fixed bed cylindrical reactor for converting organic solid waste into a solid product and a gas-liquid product mixture through pyrolysis, the reactor includes a three-zone furnace wherein each zone provides a temperature of up to 850° C., wherein the reactor includes a collection unit in direct communication therewith to collect the solid product;
   a source of carrier gas in contact with the pyrolysis reactor for achieving pyrolytic conditions therein;
   a first gas-liquid separator in fluid communication with the pyrolysis reactor and a chiller, the first gas-liquid separator receiving the gas-liquid product mixture directly from the pyrolysis reactor, separating a portion of gas therefrom, and outputting the portion of gas from the first gas-liquid separator for analysis thereof;
   a condenser receiving the gas-liquid product mixture directly from the first gas-liquid separator;
   a second gas-liquid separator in direct fluid communication with the condenser, the second gas-liquid separator receiving the gas-liquid product mixture therefrom and separating the remainder of the gas therefrom, whereby the remainder of the gas and the separated liquid are each collected separately from one another for analysis thereof; and
   a multi-port valve for separating the separated liquid into fractional components for automatic sampling of the liquid.

2. The pyrolysis reactor system as recited in claim 1, wherein said pyrolysis reactor further comprises an outlet hopper for receiving the solid product.

3. The pyrolysis reactor system as recited in claim 1, further comprising a mass flow controller in communication with said pyrolysis reactor and said source of carrier gas for selectively controlling rate of flow of the organic solid waste into said pyrolysis reactor.

4. The pyrolysis reactor system as recited in claim 1, wherein the carrier gas comprises nitrogen.

* * * * *